United States Patent [19]
Kahn et al.

[11] Patent Number: 6,083,870
[45] Date of Patent: Jul. 4, 2000

[54] ALKALINE EARTH METAL COMPOUND-SUPPORTED SILVER CATALYSTS

[75] Inventors: Andrew P. Kahn, Lafayette Hill; Anne M. Gaffney; Rangasamy Pitchai, both of West Chester, all of Pa.

[73] Assignee: ARCO Chemical Technology, L.P., Greenville, Del.

[21] Appl. No.: 09/037,441

[22] Filed: Mar. 10, 1998

Related U.S. Application Data

[62] Division of application No. 08/617,236, Mar. 18, 1996, Pat. No. 5,763,630.

[51] Int. Cl.$^7$ .............................. B01J 23/50; B01J 27/18; B01J 27/135
[52] U.S. Cl. .................. 502/340; 502/208; 502/224; 502/226; 502/227; 502/228; 502/231; 502/341; 502/344; 502/347; 502/348
[58] Field of Search ................... 502/340, 341, 502/344, 347, 348, 208, 224, 226, 227, 228, 231

[56] References Cited

U.S. PATENT DOCUMENTS

| | | | |
|---|---|---|---|
| 4,410,715 | 10/1983 | McMullin et al. | 549/531 |
| 5,145,824 | 9/1992 | Buffum et al. | 502/216 |
| 5,502,020 | 3/1996 | Iwakura et al. | 502/317 |
| 5,504,053 | 4/1996 | Chou et al. | 502/348 |
| 5,686,380 | 11/1997 | Pitchai et al. | 502/347 |

FOREIGN PATENT DOCUMENTS

| | | |
|---|---|---|
| 1282772 | 4/1991 | Canada . |
| 0393785 | 1/1995 | European Pat. Off. . |

*Primary Examiner*—Elizabeth D Wood
*Attorney, Agent, or Firm*—Stephen D. Harper; William C. Long

[57] ABSTRACT

Propylene is oxidized to propylene oxide in the vapor phase using an oxygen-containing gas and a supported silver catalyst comprising silver and a support comprised in whole or in substantial part of certain alkaline earth metal compounds. The alkaline earth metal compound may, for example, be a calcium compound such as calcium titanate, tribasic calcium phosphate, calcium molybdate, or calcium fluoride, a magnesium compound such as magnesium aluminate, or a strontium compound such as strontium titanate. Such supports provide significantly higher selectivity to the desired epoxide than would be expected from the performance of related materials. Propylene oxide selectivity may be further enhanced through the introduction of nitrogen oxide species such as NO, alkyl halides such as ethyl chloride, and carbon dioxide into the oxygen-containing gas.

12 Claims, No Drawings

ALKALINE EARTH METAL COMPOUND-SUPPORTED SILVER CATALYSTS

This is a division of application Ser. No. 08/617,236, filed Mar. 18, 1996, now U.S. Pat. No. 5,763,630.

FIELD OF THE INVENTION

This invention relates to a process for the direct oxidation of propylene to propylene oxide in the vapor phase using molecular oxygen. In particular, the invention pertains to the use of catalysts comprised of silver supported on certain alkaline earth metal-containing compounds to selectively form the epoxide.

BACKGROUND OF THE INVENTION

The direct oxidation of ethylene to ethylene oxide by molecular oxygen is well-known and is, in fact, the method used currently for commercial production of ethylene oxide. The typical catalyst for such purpose contains metallic or ionic silver, optionally modified with various promoters and activators. Most such catalysts contain a porous, inert support or carrier such as alpha alumina upon which the silver and promoters are deposited. A review of the direct oxidation of ethylene in the presence of supported silver catalysts is provided by Sachtler et al. in *Catalyst Reviews: Science and Engineering*, 23 (1&2), 127–149 (1981).

It is also well-known, however, that the catalysts and reaction conditions which are best suited for ethylene oxide production do not give comparable results in the direct oxidation of higher olefins such as propylene. The discovery of processes capable of providing propylene oxide by vapor phase direct oxidation in higher yields than are presently attainable thus would be most desirable.

New support materials are continuously being tried. However, many of those which were employed in the early development of the silver-bearing catalysts are, with some modifications, still being used. Materials which have found most widespread use are typically inorganic and generally are of a mineral nature.

Alumina, in its various forms, particularly alpha-alumina, has been preferred as a support material for silver-containing catalysts in the preparation of epoxides. Numerous variations of surface area, pore dimensions, pore volume and particle size have been suggested as providing the ideal physical property or combination of properties for improving efficiency, activity or useful life of the catalyst.

In seeking the ideal support material, there has been some departure from the commonly employed substances. For example, some use has been made of alkali metal and alkaline earth metal carbonates, both as the sole support material and in combination with other materials as the carrier for processes such as direct oxidation of alkenes to epoxides. For example, Canadian Pat. No. 1,282,772 teaches the use of alkaline earth metal carbonates as supports for silver catalysts in olefin epoxidation systems.

The development of alternative supports which provide equivalent or improved performance in epoxidation process as compared to known materials would be highly advantageous, as such alternative supports may be of lower cost or provide other practical benefits such as higher strength or structural integrity. Selecting materials which will be suitable for such purpose is not straightforward, however. For example, as will be subsequently demonstrated, not all alkaline earth metal-containing compounds perform equivalently as supports for silver epoxidation catalysts. Structurally analogous substances often exhibit radically different behavior in an epoxidation process. Predicting in advance which substances will provide the high degree of selectivity to epoxide which is required in a commercial process thus is nearly impossible.

European Pat. No. 393,785 teaches a catalyst for the manufacture of alkylene oxide containing an impregnated silver metal on an inert refractory solid support, at least one promoter to enhance the efficiency of the catalyst and a manganese component. The efficiency promoter may be a compound comprising at least one alkali metal or oxyanion of an element other than manganese or oxygen selected from group 3b through 7b and 3a through 7a of the Periodic Table; titanates and phosphates are listed as being suitable oxyanions for such purpose. A maximum of 2 weight % of the anion in the catalyst is taught. A cationic promoter such as an alkaline earth metal may also be present up to a concentration of 1 weight percent in the finished catalyst. This publication thus does not contemplate the use of alkaline earth metal titanates or phosphates as the inert refractory solid support.

SUMMARY OF THE INVENTION

This invention provides a process for propylene epoxidation wherein a feedstream comprising oxygen and propylene is contacted in the vapor phase at a temperature of 180° C. to 350° C. with a supported silver catalyst comprising silver and a support comprising an alkaline earth metal-containing compound selected from the group consisting of alkaline earth metal titanates, tribasic calcium phosphate, magnesium aluminate, calcium molybdate, calcium fluoride, and mixtures thereof.

DETAILED DESCRIPTION OF THE INVENTION

The present invention is directed to a process for the vapor phase oxidation of propylene to propylene oxide, i.e., an epoxidation process performed in the presence of molecular oxygen and a particular class of supported silver catalysts.

The support material used in the present invention is selected from one of several alkaline earth metal compound-containing carrier materials. The alkaline earth metal compound employed is an inorganic compound containing one or more alkaline earth metals, particularly calcium, strontium, magnesium or barium with calcium, strontium and barium being most preferred. Depending upon the alkaline earth metal selected, the alkaline earth metal compound may additionally contain titanate, phosphate, aluminate, molybdate, fluoride, or some combination thereof. Specifically, the alkaline earth metal compound is selected from the group consisting of alkaline earth metal titanates (e.g., calcium titanate, strontium titanate), tribasic calcium phosphate, magnesium aluminate, calcium molybdate, calcium fluoride and mixtures thereof.

Tribasic calcium phosphate is an inorganic substance corresponding to the approximate empirical formula $Ca_{10}(OH)_2(PO_4)_6$, containing 34–40% Ca, and having the CAS Registry number CAS 12167-74-7. As will be demonstrated subsequently in the examples, tribasic calcium phosphate has unexpectedly been found to be far superior as a support material than related substances such as tricalcium phosphate (CAS 7758-87-4) and hydroxyapatite (CAS 1306-06-5).

Calcium molybdate is the calcium salt of molybdic acid and has the chemical composition $CaMoO_4$.

Calcium fluoride has the chemical composition $CaF_2$ and is found in nature as fluorite (pure form) or fluorspar (mineral), but may also be prepared synthetically by the reaction of a soluble calcium salt and sodium fluoride.

Magnesium aluminate is an oxide of magnesium and aluminum corresponding approximately to the empirical formula $MgO.Al_2O_3$.

Alkaline earth metal titanates comprise the class of inorganic substances containing an alkaline earth metal such as barium, strontium, calcium or magnesium and a titanate species. Suitable alkaline earth metal titanates thus may correspond to the empirical formula $MTiO_3$, $M_2TiO_4$, and $MTi_2O_5$ wherein M preferably=Ba, Sr, Ca, or Mg. Any of the conventional methods for preparing such substances may be utilized. Barium titanate, for example, may be prepared by heating a mixture of the correct proportions of barium carbonate and titanium dioxide at 1300° C. until the reaction is complete. Strontium titanate may be obtained in pure form by calcining the double strontium titanium oxalate precipitate from titanium tetrachloride solution. The calcium titanate can correspond to the compound $CaTio_3$ (12049-50-2), which occurs naturally as the mineral perovskite, but which can also be synthesized by heating equimolar amounts of the oxide to 1350° C. The term "calcium titanate" as used herein also embraces the substances having the formula $3CaO.2TiO_2$ (CAS 12013-80-8) and $3CaO.TiO$ (CAS 12013-70-6). Magnesium titanates include the metatitanate $MgTiO_3$, the orthotitanate $Mg_2TiO_4$, and the dititanate $MgTi_2O_5$.

Such support materials are capable of providing exceptionally high propylene oxide selectivities and have been found to be surprisingly superior to other support materials in this respect. The carriers of the present invention may exist in various forms. In one embodiment, the carrier is one in which the alkaline earth metal compound is the predominate (i.e., at least 50% by weight) or, preferably, substantially the exclusive component of the support (i.e., the support consists essentially of one or more alkaline earth metal compounds). In other embodiments of the invention, the inorganic support material is used in conjunction with a solid substrate, i.e., a subsupport or substructure composed of a more conventional support material, such as alumina (preferably, alpha-alumina). This latter type of support may employ the alkaline earth metal compound material coated on individual, relatively small particles of substructure or subsupport or on a larger unit such as a three-dimensional framework having a honeycomb-type of structure. However, the alkaline earth metal compound support material will comprise at least 25 weight percent (in some embodiments, at least 35 weight percent) of the finished catalyst. The concentrations of alkaline earth metal compounds in the catalysts of the present invention thus are considerably greater than the amounts of compounds typically utilized by prior workers as promoters in supported silver catalysts.

A granular form of the alkaline earth metal carbonate support material is preferred in the present invention, particularly when used as the exclusive or predominant component of the support. Alkaline earth metal carbonate materials suitable for use in the present invention may be commercially obtained as powders which can be converted to the preferred granular form by conventional methods. As described in greater detail below, the granular support may then be impregnated, or coated, with a solution containing a silver compound and thereafter reduced to elemental silver.

Alternatively, as described below, the powdered granular support material may be combined with an appropriate silver-containing solution, such as that used conventionally to impregnate solid supports to form a slurry or paste. This material may then be spread on a suitable surface and dried and calcined at an appropriate temperature, such as about 500° C. This results in an alkaline earth metal compound support with silver being supported thereon in its elemental state. The catalyst may then be impregnated with solutions of promoters, modifiers, co-catalysts or other additives of the types well known in the supported silver oxidation catalyst art (hereinafter referred to collectively as "promoters"), if so desired and thereafter dried. As an alternative, promoters may be dissolved in the same silver-containing impregnation solution used to form the coating paste or slurry with the alkaline earth metal compound material.

The support material, before or after incorporation of the silver and optional promoter(s), can be formed into shaped composites suitable for use in propylene oxide manufacture. The composites may be formed by any suitable technique. For instance, it is possible to form the composites by compressing the support materials into a mold having a desired configuration. The size of the particles may be selected to be appropriate for the formation of the composite and are often in the range of about 0.001 to about 5 millimeters in major dimension.

When coated catalysts, i.e., those catalysts in which the alkaline earth metal compound material is coated on a substructure are employed, a slurry of said material, in either powder or granular form, may be mixed with the particles of substructure support material and thereafter dried. As with the predominant or exclusive alkaline earth metal compound support materials described above, the coated catalysts may also be prepared by using a solution of a silver compound and any promoter or the like which may be desired or separate solutions of silver compound and promoter(s) to form the slurry, followed by suitable drying and calcination.

The surface area of the alkaline earth metal compound support material generally is at least 0.6 $m^2/g$, preferably at least 1.5 $m^2/g$. However, alkaline earth metal compound support materials having relatively high surface areas are also effective for the purposes of this invention. For instance, tribasic calcium phosphate support materials having surface areas of 50 to 100 $m^2/g$ have been found to function quite effectively in the present invention. This finding was unexpected in view of the fact that support materials such as alpha alumina which are conventionally used for silver vapor phase oxidation catalysts preferably have much lower surface areas. The surface area is measured by the conventional B. E. T. method using nitrogen or krypton described by Brunauer, Emmett and Teller in *J. Am. Chem. Soc.* 60, 309–16 (1938).

The support materials used in the present invention may generally be described as porous or microporous and typically have water pore volumes of about 0.05 to 0.80 cc/g.

The supported silver catalysts are typically used as individual particles of irregular shape and size. This is true both for the predominate or exclusive alkaline earth metal compound supports as well as the alkaline earth metal compound-coated supports. However, in some instances the supports, particularly the coated supports, may have a particular shape and size and this is especially true of the subsupports used with the alkaline earth metal compound. Typically the subsupports are formed into aggregates or "pills" of a size and configuration to be usable in tubular reactors. These pills may be formed by conventional extrusion and firing techniques. The pills generally range in size from about 2 mm to about 15 mm, preferably about 3 mm to about 12 mm. The size is chosen to be consistent with the type of reactor employed. For example, in fixed bed reactor applications, sizes ranging from about 3 mm to about 10 mm have been found to be most suitable in the tubular reactors commonly utilized. The shapes of the carrier aggregates useful for purposes of the present invention can vary widely and can be any of the forms conventionally used in the heterogeneous catalyst art.

The alkaline earth metal compound- and alkaline earth metal compound-coated supports may be prepared as indicated above or obtained commercially. The carbonate-supported catalyst of the present invention may be prepared by any known method of introducing silver and/or a promoter in soluble form, to a support. A preferred method of introducing silver to the alkaline earth metal compound support is by an impregnation process in which a solution of a soluble salt or silver compound (which can be a salt or complex of silver) in an amount sufficient to deposit the desired weight of silver upon the carrier is dissolved in a suitable solvent or "complexing/solubilizing" agent. The solution may be used to impregnate the support or carrier by immersing the carrier in the silver-containing impregnating solution and forming a pasty mixture or slurry. The slurry is then dried and calcined by placing the mixture in an oven or furnace at about 100 to about 120° C. for 0.5 to 6 hours and then heating the mixture at a temperature of from about 250 to about 600° C. for another 1 to 6 hours. This procedure accomplishes drying of the alkaline earth metal compound/silver mixture, removes volatile components and reduces the silver present to its elemental form.

Selectivity to the desired propylene oxide product may be further optimized by the incorporation of one or more promoters, additives, co-catalysts, modifying agents or the like into the supported silver catalyst. In one desirable embodiment, the catalyst contains not only an alkaline earth metal compound support and silver but also a potassium salt.

The optional potassium salt may be introduced to the catalyst as an impregnation solution in a separate impregnation step. Again, this may be done by any known manner of impregnating a porous material. Conveniently, this may be carried out by placing the catalyst material in a container, evacuating the container and thereafter introducing the salt solution. Alternatively, the support may be sprayed or sprinkled with the impregnating solution. The excess solution may then be allowed to drain off or the solvent may be removed by evaporation under reduced pressure at a suitable temperature. The catalyst may then be dried at a moderate temperature (e.g., at 120° C.) in a oven for one-half to five hours. Such a procedure is known as a "sequential" or "consecutive" method of preparation. The alkaline earth metal compound-supported catalyst may also be prepared by a "simultaneous" or "coincidental" method of preparation. With this method, the potassium salt is included in the silver compound-containing solution used to impregnate the support.

The alkaline earth metal compound-coated catalysts are prepared by coating a suitable substructure or subsupport material, preferably alumina, and most preferably alpha alumina, with an alkaline earth metal compound-containing slurry. This may contain only the alkaline earth metal compound, in which case the coated support is further treated as indicated above to produce a silver or a silver and promoter alkaline earth metal compound-coated catalyst. Alternatively, an alkaline earth metal compound/silver compound slurry or an alkaline earth metal compound/silver compound/promoter slurry may be produced in a sequential or coincidental procedure. Thus, in a sequential procedure, particles or pills of a suitable subsupport material, such as alpha-alumina, are coated with a slurry of an alkaline earth metal compound material and a soluble salt or complex of silver dissolved in a complexing/solubilizing agent. The particles or pills are thereafter drained and calcined in an oven at a temperature of about 250° C. to about 600° C. for about three minutes to about four hours, the duration of heating being in general inversely proportional to the temperature employed. The catalyst is then impregnated in the manner described above with a solution of promoter, and then dried. The alkaline earth metal compound-coated supports may also be formed by a coincidental procedure in which an alkaline earth metal compound/silver compound/promoter slurry is used to coat particles or pills of a suitable subsupport. After draining, the catalyst is dried at a temperature and for a duration indicated above for those carbonate-coated catalysts prepared by the sequential procedure. The particular silver salt or compound used to form the silver-containing impregnating solution in a solvent or a complexing/solubilizing agent is not particularly critical and any silver salt or compound generally known to the art which is both soluble in and does not react with the solvent or complexing/solubilizing agent to form an unwanted product may be employed. Thus, the silver may be introduced to the solvent or complexing/solubilizing agent as an oxide or a salt, such as nitrate, carbonate, or carboxylate, for example, an acetate, propionate, butyrate, oxalate, malonate, malate, maleate, lactate, citrate, phthalate, fatty acid ester, and the like or combinations thereof.

A large number of solvents or complexing/solubilizing agents may be suitably used to form the silver-containing impregnating solution. Besides adequately dissolving the silver or converting it to a soluble form, a suitable solvent or complexing/solubilizing agent should be capable of being readily removed in subsequent steps, either by a washing, volatilizing or oxidation procedure, or the like. The complexing/solubilizing agent, preferably, should also permit solution to provide silver in the finished catalyst to the extent of preferably about 25 to about 60 percent silver, based on the total weight of the catalyst. It is also generally preferred that the solvents or complexing/solubilizing agents be readily miscible with water since aqueous solutions may be conveniently employed. Among the materials found suitable as solvents or complexing/solubilizing agents for the preparation of the silver-containing solutions are alcohols, including glycols, such as ethylene glycol, amines (including alkanolamines and alkyldiamines) and carboxylic acids, such as lactic acid and oxalic acid, as well as aqueous mixtures of such materials.

Typically, a silver-containing solution is prepared by dissolving silver in a suitable solvent or complexing/solubilizing agent such as, for example, a mixture of water, ethylenediamine, oxalic acid, silver oxide, and monoethanolamine. The solution is then mixed with support particles and drained. Thereafter the particles are suitably dried.

As indicated above, after impregnation, the silver-impregnated support particles are treated to convert the silver salt or complex to silver metal and thereby effect deposition of silver on the surface of the support. As used herein, the term "surface", as applied to the support, includes not only the external surfaces of the support but also the internal surfaces, that is, the surfaces defining the pores or internal portion of the support particles. This may be done by treating the impregnated particles with a reducing agent, such as hydrogen or hydrazine and/or by roasting, at an elevated temperature to decompose the silver compound and reduce the silver to its free metallic state. Certain solubilizing agents such as alkanolamines, alkyldiamines, and the like may also function as reducing agents.

Although at least a catalytically effective amount of silver must be present in the finished catalyst (meaning an amount that provides a measurable conversion of propylene to propylene oxide), the silver concentration preferably is from about 2 percent to 70 percent, by weight, based on the total weight of the catalyst. More preferably, the silver concentration ranges from about 25 to 60 percent by weight.

It has been discovered that the presence of certain specific potassium salts in the supported silver catalyst significantly enhances the efficiency of said catalyst as a propylene epoxidation catalyst. The anion preferably is a nitrogen oxyanion (i.e., an anion or negative ion which contains both nitrogen and oxygen atoms) such as nitrate and nitrite or a precursor thereof (i.e., an anion capable of undergoing displacement or other chemical reaction and forming a nitrogen oxyanion under epoxidation or catalyst preparation conditions). Potassium nitrate ($KNO_3$) is the preferred potassium salt. Halide salts of potassium such as potassium fluoride may also be employed, as halide has been found to function as a precursor to nitrate (i.e., is converted to nitrate under the epoxidation conditions).

The efficiency-enhancing potassium salt may be introduced to the catalyst in any known manner. Thus, impregnation and deposition of silver and a potassium salt may be effected coincidentally or sequentially, as described above.

In order to perform coincidental impregnation, the potassium salt must be soluble in the same solvent or complexing/solubilizing liquid used with the silver impregnating solution. With the preferred sequential procedure in which the silver is added first, any solvent capable of dissolving the salt which will neither react with the silver nor leach it from the support is suitable. Aqueous solutions are generally preferred, but organic liquids, such as alcohols, may also be employed. Suitable procedures for effecting introduction of the potassium salt to the solid support are well known in the art.

The optional potassium salt is added in an amount sufficient to provide an improvement in one or more of the catalytic properties (e.g., selectivity, activity, conversion, stability, yield) of the supported silver catalyst as compared to a catalyst not containing the potassium salt (herein referred to as "promoting amount"). The precise amount will vary depending upon such variables as the nitrogen oxide species and concentration thereof employed in the epoxidation procedure, the concentration of other components in the feed stream, the amount of silver contained in the catalyst, the surface area of the support, the process conditions, e.g., space velocity and temperature, and morphology of support. Generally, however, a suitable concentration range of the added potassium salt, calculated as cation, is about 0.15 to about 5 percent, preferably about 0.5 to about 3 percent, by weight, based on the total weight of the catalyst. Most preferably, the salt is added in an amount of about 1.5 to about 2.5 weight percent K.

Propylene and an oxygen-containing gas (i.e., a gas comprising molecular oxygen) are brought together in a reactor in the presence of the previously described catalyst under conditions effective to accomplish at least partial epoxidation of the propylene. Typical epoxidation conditions include temperatures within the reaction zone of the reactor on the order of about 180 to 350° C. (more preferably, 200 to 300° C.) and pressures from about 1 to about 30 atmospheres. Inlet pressures may be as low as 14 to 75 psig. To favor high selectivity to epoxide, it is desirable that the feed stream contain carbon dioxide and/or an organic halide (described in more detail hereafter). A gaseous nitrogen oxide species (described in more detail hereafter) may also optionally be supplied to the reaction zone within the reactor by introducing said species to the feedstream containing propylene (fresh and/or recycled) and molecular oxygen.

Examples of nitrogen oxide species suitable for optional introduction in the feedstream include at least one of NO, $NO_2$, $N_2O_4$, $N_2O_3$ or any gaseous substance capable of forming one of the aforementioned gases, particularly NO and $NO_2$, under epoxidation conditions, and mixtures of one of the foregoing, particularly NO, with one or more of CO, $PH_3$, $SO_3$ and $SO_2$. NO is the most preferred nitrogen oxide species. Inclusion of such nitrogen oxide species in the feedstream is not necessary, however.

The amount of gaseous nitrogen oxide species present (if any) is not critical. The optimum amount is determined, in part, by the particular potassium salt used and the concentration thereof, and by other factors noted above which influence the optimum amount of potassium salt. Typically, a suitable concentration of the nitrogen oxide species for epoxidation of propylene, is about 0.1 to about 2,000 ppm, by volume, when $N_2$ is used as ballast. When NO is used in the epoxidation of propylene, the preferred concentration is about 5 to about 2,000 ppm, more preferably about 20 to 500 ppm, by volume, with an $N_2$ ballast. However, as explained previously, the nitrogen oxide species concentration may be essentially zero.

The "oxygen" employed in the reaction may be defined as including pure molecular oxygen, atomic oxygen, any transient radical species derived from atomic or molecular oxygen capable of existence under epoxidation conditions, mixtures of another gaseous substance with at least one of the foregoing, and substances capable of forming one of the foregoing under epoxidation conditions. The oxygen is typically introduced to the reactor either as air, commercially pure oxygen or other substance which under epoxidation conditions both exists in a gaseous state and forms molecular oxygen.

The gaseous components which are supplied to the reaction zone, or that region of the reactor where reactants and catalyst are brought together under epoxidation conditions, are generally combined before being introduced to the reactor. If desired, however, such components may alternatively be introduced separately or in various combinations. The feed stream having the particular composition previously described thus may be formed prior to or at the time the individual components thereof enter the reaction zone. The use of term "feedstream" herein thus is not meant to limit the present process to the embodiment where all of the gaseous components are combined prior to introduction of said components into the reaction zone. The reactors in which the process and catalyst of the present invention are employed may be of any type known to the art. A brief description of several of the reactor parameters which may be used in the present invention is presented below.

In addition to propylene and oxygen (and, optionally, a nitrogen oxide species), the feedstream also desirably contains a performance-enhancing organic halide such as an alkyl halide. The organic halide is preferably a volatile compound, i.e., a substance which predominantly exists in gaseous form under the temperature and pressure conditions present in the reaction zone. The normal boiling point of the organic halide is most preferably less than about 100° C. at atmospheric pressure. Compounds containing from 1 to 10 carbon atoms are preferred. Most preferably, the alkyl halide is a chloride species. The term alkyl halide includes both saturated and unsaturated halides, such as ethylene dichloride, ethyl chloride, vinyl chloride, methyl chloride and methylene chloride. Preferably, ethyl chloride is employed as the organic halide. Mixtures of different organic halides may be employed. The amount of organic halide employed will vary depending upon a variety of factors, including the concentration of propylene being oxidized, the particular catalyst promoter(s) and nitrogen oxide species and the concentrations thereof, as well as other factors noted above as influencing the optimum amount of potassium salt and nitrogen oxide species. However, a suitable range of concentration for the organic halide in the oxidation of propylene is typically about 0.1 to about 2,000 ppm, more preferably about 25 to 500 ppm by volume, of the feedstream. In addition, a hydrocarbon, particularly a saturated hydrocarbon, such as methane, propane, or ethane, may be included in the feedstream. The feedstream may also contain a ballast or diluent, such as nitrogen, or other inert gas, particularly when air is used as the oxygen-containing gas. Varying amounts of water vapor may also be present.

Carbon dioxide is also desirable to include as a component of the feedstream in the epoxidation process of this invention. The presence of carbon dioxide, within certain limits, has been found to provide surprising improvement in propylene oxide selectivity. Desirable enhancements in selectivity are generally observed using 1 to 60 volume % $CO_2$ in the feedstream, with 5 to 25 volume % $CO_2$ being preferred.

The components of the feedstream are most suitably present in the amounts shown in the following table.

| Component | Volume in % (or ppm) for Propylene Oxidation |
| --- | --- |
| propylene | about 2 to about 50% |
| oxygen | about 2 to about 10% |
| organic halide | 0 to about 2,000 ppm, more preferably, about 20 to 500 ppm |
| nitrogen oxide species | 0 to about 2,000 ppm |
| hydrocarbon other than propylene | 0 to about 5% |
| carbon dioxide | 0 to 60%, more preferably 5 to 25% |
| nitrogen or other ballast gas | remainder. |

Although the present invention can be used with any size and type of vapor phase epoxidation reactor, including both fixed bed and fluidized bed reactors known to the art, it is contemplated that the present invention will find most widespread application in standard fixed bed, multi-tubular reactors such as those now in use as ethylene oxide reactors. These generally include wall-cooled as well as adiabatic or non-wall-cooled reactors. Tube lengths may typically range from about 5 to about 60 feet but will frequently be in the range of from about 15 to about 45 feet. The tubes may have internal diameters from about 0.5 to about 2.5 inches and are expected to be typically from about 0.8 to about 1.5 inches. A plurality of tubes packed with catalyst arranged in parallel within a suitable shell may be employed. GHSV generally range from about 500 to about 10,000 $hr^{-1}$. Typically GHSV values range from about 800 to about 3,000 $hours^{-1}$ at pressures from about 1 to about 30 atmospheres, commonly about 1.1 to about 5 atmospheres. Contact times should be sufficient to convert 0.5 to 70%, preferably 5 to 30%, of the propylene.

EXAMPLES

Example 1

A supported silver catalyst in accordance with the invention comprising 39 weight % Ag and 1.9 weight % K on a tribasic calcium phosphate support (Aldrich; CAS 12167-74-7; surface area=65 $m^2/g$) was prepared in accordance with the following procedure: A 4 oz. jar was charged with ceramic stones (5), ethylene diamine (10.30 g), distilled water (10.20 g), oxalic acid dihydrate (7.50 g), silver (I) oxide (13.0 g), monoethanolamine (3.63 g), potassium nitrate (1.59 g) in distilled water (5.17 g), and the tribasic calcium phosphate (17.0 g). The jar was sealed and placed on a ball mill for 4 hours. The resulting mixture was dried at 110° C. for 1 hour and then calcined at 300° C. for hours. The material was thereafter pelletized and sieved to 14/30 mesh. The supported silver catalyst was tested for activity in propylene oxidation using a tubular reactor under the following run conditions: 2 cc catalyst, 10 volume % propylene, 5 volume % oxygen, 50 ppm ethyl chloride, 200 ppm NO, GHSV=1200 $hr^{-1}$, 40 cc/min flow rate, 30 psig, 250° C. Propylene conversion of 5% with selectivity to propylene oxide of 27% were obtained. Increasing the concentration of ethyl chloride to 200 ppm improved the propylene selectivity to 34% (5% propylene conversion).

Example 2

A supported silver catalyst in accordance with the invention comprising 41 weight % Ag and 2 weight %K (added as KF) on a tribasic calcium phosphate support (Aldrich; CAS 12167-74-7; surface area=65 $m^2/g$) was tested for activity in propylene oxidation using a tubular reactor using the same run conditions as described in Example 1 (50 ppm ethyl chloride). Propylene selectivity of 36% at 6% propylene conversion was observed.

The following Comparative Examples 1–4 demonstrate the superiority of tribasic calcium phosphate as a catalyst support over other substances which also contain calcium and phosphate components.

Comparative Example 1

A supported silver catalyst comprising 40 weight % Ag and 2 weight % K (added as $KNO_3$) on a monobasic calcium phosphate (CAS 7758-23-8) support was prepared and tested for activity using the run conditions described in Example 1 (50 ppm ethyl chloride; 40 psig). Only 1% propylene conversion was achieved; no propylene oxide was detected.

Comparative Example 2

A supported silver catalyst comprising 39 weight % Ag and 1.9 weight % K (added as $KNO_3$) on a dibasic calcium phosphate (CAS 7757-93-9) support was prepared and tested for activity in propylene oxidation using the same conditions as in Example 1. As in Comparative Example 1, no propylene oxide was detected and the propylene conversion was low (1%).

Comparative Example 3

A supported silver catalyst comprising 43 weight % Ag and 2 weight % K (added as $KNO_3$) on a hydroxyapatite support (CAS 1306-06-5; surface area=33 $m^2/g$) was prepared and tested for activity in propylene oxidation under the run conditions of Comparative Example 1. The results obtained (1% propylene conversion; 0% propylene oxide selectivity) provide further confirmation of the superiority of tribasic calcium phosphate as a catalyst support.

Comparative Example 4

A supported silver catalyst comprising 43 weight % Ag and 2.1 weight % K (added as $KNO_3$) on a tricalcium phosphate support (CAS 7758-87-4; surface area=47 m²/g) was prepared and evaluated for activity as a propylene oxidation catalyst using the conditions described in Example 1 (50 ppm EtCl). Surprisingly, despite the compositional similarities between tribasic calcium phosphate and tricalcium phosphate, the latter compound when used as a support gave no detectable propylene oxide and only 1% conversion of propylene.

Example 3

A supported silver catalyst in accordance with the invention comprising 39 weight % Ag and 2.1 weight % K (added as $KNO_3$) on a calcium fluoride support was prepared and tested for activity in propylene oxidation using the same condition described in Example 1 (50 ppm ethyl chloride). Propylene conversion was 4%; selectivity to propylene oxide was 35%. When the $O_2$ level was increased to 8 volume %, propylene conversion was 7% and propylene oxide selectivity improved to 40%.

Example 4

A supported silver catalyst in accordance with the invention comprising 50 weight % Ag and 2 weight % K (added as $KNO_3$) on a magnesium aluminate support was prepared and tested for activity in propylene oxidation using the same conditions described in Example 1 (50 ppm ethyl chloride; 50 volume % $CO_2$). Propylene conversion was 6%; propylene oxide selectivity was 42%.

Example 5

A supported silver catalyst in accordance with the invention comprising 50 weight % Ag and 1.3 weight % K (added as $KNO_3$) on a strontium titanate support was prepared and tested for activity in propylene oxidation using the same conditions described in Example 1 (50 ppm ethyl chloride). At 10% propylene conversion, propylene oxide selectivity was 38%.

Example 6

A supported silver catalyst in accordance with the invention comprising 54 weight % Ag and 1.9 weight % K (added as $KNO_3$) on a calcium molybdate support was prepared and tested for activity in propylene oxidation using run conditions identical to those of Example 1 (50 ppm ethyl chloride). Propylene conversion was 2%; selectivity to propylene oxide was 26%.

Example 7

A supported silver catalyst in accordance with the invention comprising 43 weight % Ag and 1.6 weight % K (added as $KNO_3$) on a calcium titanate support was prepared and tested for activity in propylene oxidation using the same conditions described in Example 1 except for the use of 200 ppm ethyl chloride. Propylene oxide selectivity of 36% at 4% propylene conversion was observed.

Example 8

A supported silver catalyst in accordance with the invention comprising 42 weight % Ag and 1.1 weight % K (added as $KNO_3$) on a barium titanate support was prepared and tested for activity in propylene oxidation using the same conditions described in Example 1 except for the use of 200 ppm ethyl chloride. Propylene oxide selectivity of 26% at 3% propylene conversion was observed.

Example 9

A supported silver catalyst in accordance with the invention comprising 50 weight % Ag and 1.5 weight % K (added as $KNO_3$) on a magnesium titanate support was prepared and tested for activity in propylene oxidation using the same conditions as described in Example 1 except for the use of 200 ppm ethyl chloride. Propylene oxide selectivity of 35% at 4% propylene conversion was observed.

We claim:

1. A supported silver catalyst useful for propylene epoxidation comprising silver and a support comprising an alkaline earth metal-containing compound selected from the group consisting of alkaline earth metal titanates, tribasic calcium phosphate, magnesium aluminate, calcium molybdate, calcium fluoride, and mixtures thereof, the alkaline earth metal-containing compound comprising at least 25% by weight of the supported catalyst.

2. The supported silver catalyst of claim 1, which is additionally comprised of a potassium salt comprising potassium cation and an anion selected from the group consisting of nitrate, nitrite, anions capable of forming nitrate under the epoxidation conditions and mixtures thereof.

3. The supported silver catalyst of claim 1 wherein the support is additionally comprised of an inert refractory solid support other than the alkaline earth metal-containing compound.

4. The supported silver catalyst of claim 1 wherein the support consists essentially of the alkaline earth metal-containing compound.

5. The supported silver catalyst of claim 1 wherein the alkaline earth metal-containing compound comprises at least 35 wt % of the supported silver catalyst.

6. The supported silver catalyst of claim 1 wherein silver comprises from 25 to 60 wt % of the supported silver catalyst.

7. A supported silver catalyst useful for propylene epoxidation comprising from 25 to 60 wt % silver, a support comprising an alkaline earth metal-containing compound selected from the group consisting of strontium titanate, calcium titanate, barium titanate, magnesium titanate, tribasic calcium phosphate, magnesium aluminate, calcium molybdate, calcium fluoride and mixtures thereof, the alkaline earth metal-containing compound comprising at least 35 wt % of the supported silver catalyst, and a potassium salt comprising potassium cation and an anion selected from the group consisting of nitrate, nitrite, anions capable of forming nitrate under epoxidation conditions, and mixtures thereof.

8. The supported silver catalyst of claim 7 wherein the potassium salt is potassium nitrate.

9. The supported silver catalyst of claim 7 wherein the potassium salt is present in an amount corresponding to 0.5 to 3 wt %, calculated as potassium cation, of the supported silver catalyst.

10. The supported silver catalyst of claim 7 wherein the support is additionally comprised of an inert refractory solid support other than the alkaline earth metal-containing compound.

11. The supported silver catalyst of claim 10 wherein the inert refractory solid support is alumina.

12. The supported silver catalyst of claim 8 wherein the support consists essentially of the alkaline earth metal-containing compound.

* * * * *